United States Patent
Bedding et al.

(10) Patent No.: US 7,824,706 B2
(45) Date of Patent: *Nov. 2, 2010

(54) DIETARY SUPPLEMENT AND METHOD FOR THE TREATMENT OF DIGESTIVE TRACT ULCERS IN EQUINES

(75) Inventors: Peter M. J. Bedding, Crediton (GB); Franklin L. Pellegrini, Streetsboro, OH (US)

(73) Assignee: Freedom Health, LLC, Aurora, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/435,367

(22) Filed: May 9, 2003

(65) Prior Publication Data

US 2004/0224036 A1    Nov. 11, 2004

(51) Int. Cl.
- A23K 1/17      (2006.01)
- A23K 1/165     (2006.01)
- A23K 1/18      (2006.01)
- A61K 47/00     (2006.01)
- A61K 9/28      (2006.01)
- A61K 9/68      (2006.01)

(52) U.S. Cl. ............ 424/442; 424/439; 424/438; 424/441

(58) Field of Classification Search ........ 424/400, 424/489, 438, 442, 439, 441
See application file for complete search history.

(56) References Cited

U.S. PATENT DOCUMENTS

| | | | |
|---|---|---|---|
| 4,053,492 A | * | 10/1977 | Brooke et al. ........ 554/11 |
| 4,092,431 A | * | 5/1978 | Mori et al. ........ 514/616 |
| 4,729,896 A | * | 3/1988 | Sawhill ........ 426/2 |
| 4,820,731 A | | 4/1989 | Mascioli et al. |
| 4,950,656 A | | 8/1990 | Lichtenberger |
| 5,320,846 A | | 6/1994 | Bistrian et al. |

(Continued)

FOREIGN PATENT DOCUMENTS

JP    50-5568    5/1973

(Continued)

OTHER PUBLICATIONS

"Effect of varying content of soluble dietary fiber from wheat flour and oat milling fractions on gastric emptying in pigs" by Johansen et al., British Journal of Nutrition (1996), 75, 339-3351.*

(Continued)

*Primary Examiner*—Isis A Ghali
(74) *Attorney, Agent, or Firm*—Reinhart Boerner Van Deuren s.c.

(57) ABSTRACT

A novel dietary supplement and nutritional aid and methods for the manufacture and administration of the same are disclosed for the efficacious treatment and/or prevention of digestive tract ulcers in horses and other animals. The dietary supplement of the present invention is effective in treating and/or preventing gastric ulcers, and in treating colonic ulcers as well. The dietary supplement of the present invention consists of safe and natural ingredients rather than drugs, and is orally administrable. The ingredients of the dietary supplement of the present invention when combined provide a synergistic efficacy which greatly exceeds the sum of the efficacies of the individual ingredients, making the dietary supplement highly effective in the treatment of digestive tract ulcers.

43 Claims, 1 Drawing Sheet

U.S. PATENT DOCUMENTS

| | | | |
|---|---|---|---|
| 5,505,968 A * | 4/1996 | Schaefer et al. | 424/617 |
| 5,589,186 A | 12/1996 | Isobe et al. | |
| 5,660,852 A * | 8/1997 | McKeown et al. | 424/438 |
| 5,716,639 A | 2/1998 | Carlsson et al. | |
| 5,759,537 A | 6/1998 | Garnett | |
| 5,972,985 A | 10/1999 | Thomas et al. | |
| 5,976,579 A * | 11/1999 | McLean | 424/692 |
| 6,019,995 A | 2/2000 | Steensma | |
| 6,020,324 A | 2/2000 | James et al. | |
| 6,045,834 A * | 4/2000 | Howes et al. | 426/2 |
| 6,117,458 A | 9/2000 | Morgan | |
| 6,156,355 A | 12/2000 | Shields et al. | |
| 6,200,624 B1 | 3/2001 | Mazer et al. | |
| 6,203,818 B1 | 3/2001 | Vester | |
| 6,329,414 B1 | 12/2001 | Thomas et al. | |
| 6,344,221 B1 | 2/2002 | Evans | |
| 6,355,693 B1 | 3/2002 | Herslöf et al. | |
| 6,410,067 B1 * | 6/2002 | Kanter et al. | 426/272 |
| 6,451,370 B1 | 9/2002 | Anderson | |
| 6,537,544 B1 | 3/2003 | Johansson et al. | |
| 6,759,064 B2 | 7/2004 | Morré et al. | |
| 2002/0044988 A1 * | 4/2002 | Fuchs et al. | 426/2 |
| 2003/0165604 A1 | 9/2003 | Tsubaki et al. | |

FOREIGN PATENT DOCUMENTS

| | | |
|---|---|---|
| JP | 09-262061 | 10/1997 |
| JP | 2004051582 | 2/2004 |
| WO | 9839980 | 9/1998 |
| WO | 9901044 | 1/1999 |
| WO | WO 99/18188 | 4/1999 |
| WO | WO 9918188 A1 * | 4/1999 |
| WO | 9953772 | 10/1999 |
| WO | 0117366 | 3/2001 |
| WO | WO 0174173 | 10/2001 |
| WO | WO 2005002367 | 1/2005 |

OTHER PUBLICATIONS

Equilibra 500 product information, 1989.*
"Arteriovenous difference for glutamine in equine gastrointestinal tract" by Duckworth et al. AM J Vet Res, vol. 53, No. 10, Oct. 1992.*
"What are Nutricines?", by Dr, Clifford A. Adams, copyright 2002.*
"Effect of varying content of soluble dietary fibre from wheat flour and oat milling fractions on gastric emptying in pigs" by Johansen et al.; British Journal of nurtition (1996), 75, 339-351.*
Hallfrisch et al. "Diet containing soluble oat extracts improve glucose and insulin responses of moderately hypercholesterolemic men and women", Am J Cln Nutr, 1995;61:397-84.*
Bengmark et al. "Gastroinstestinal surface protection and mucosa reconditioning"; JPEN J Partenter Enteral Nutr. Sep.-Oct. 1995; 19(5) : 410-5.*
The Random House College Dictionary, Revised Edition, Random House, Inc., 1975, p. 490.*
"β-Glucan", website at www.Isbu.ac.uk/water/hygly, pp. 1-2.
"Frequently Asked Questions About Beta Glucan 1, 3 D Glucan", About betaglucan.com website, pp. 1-4.
"Strengthening My Immune System With Beta Glucan", About betaglucan.com website, pp. 1-5.
"Gastric Ulcers in Horses: A Widespread but Manageable Disease", www.equinecentre.com.au/health_diseases_ulcers.shtml, pp. 1-4.
"Triple Crown Horse Feeds: Equimix Technology", www.triplecrownfeed.com/equimixtech.php, pp. 1-4.
"Ultra Mannan Oligosaccharide", www.ultrateck.net/petfood/yeasts.html, pp. 1-2.
"DevRx Laboratories, Inc. makes horses healthier with BioEquine™!" horses.about.com/cs/news/a/bioequine1592.html.
Miller, Alan L., ND, "Therapeutic Considerations of L-Glutamine: A Review of Literature", www.thorne.com/altmedrev/fulltext/glutamine4-4.html, Dec. 2002, pp. 1-12.
"Power Plus™ L-Glutamine: Body Builders Love Our L-Glutamine" www.pricespower.com/lglutamine, pp. 1-6.
"A Bit About Our Products: Hyaluronic Acids", www.kemme.ca/prodmain.html, pp. 1-4.
"DrHormone.com—Vitamins and Supplements", www.schwarzbeinprinciple.com/pgs/vitamins_01.html, pp. 1-5.
"Single Amino Acids", www.intensivenutrition.com/SingleAminoAcids.htm, pp. 1-5.
"Solgar Amino Acids", www.allabout-solgar-vitamins.com/solgar-amino-acids.html. pp. 1-4.
Briggs, Karen, "Provided By: The Horse Interactive Malicious Mycotoxins", www.thehorse.com/print.asp?fid=3695, pp. 1-4.
"Frequently Asked Questions: How Common is EGUS?", gastrogard.us.merial.com/faq.asp, pp. 1-4.
"Sites of Drug Action", www.egus.org/vet/treatment4.htm, pp. 1-3.
"The Truth: About Beta Glucan Products", www.beta-glucan-13d.com, pp. 1-4.
Lanigan, A.J., "Uptake Mechanism of Beta Glucan", www.Beta-glucan-13d.com/beta-glucan-mechanism.htm, pp. 102.
"Beta Glucan Research—*Saccharomyces cerevisiae*", ww.betaglucan.org, pp. 1-7.
"β-glucan", www.ceapro.com/_pages/Beta_glucan.htm, one page.
"Phospholipids", users.rcn.com/jkimball.ma.ultranet/BiologyPages/P/Phospholipids.html, one page.
"Oligosaccharide", encarta.msn.com/encnet/features/dictionary/DictionaryResults.aspx?refid=1861634848, one page.
"Re: ProfHeath—membrane synthesis", 216.239.33.100/search?q=cache:H3_DvEn0rMEC:www.cquest.utoronto.ca/botany/bio250y/talk/lectures/lec3/messages.html, one page.
Russett, Dr. J.C., "Specialty Products Research Notes: Lecithin and Equine Ulcers", Central Soya, LEC-H-55, Mar. 2002, pp. 1-10.
"L-Threonine", www.ajinomoto.co.jp/ajinomoto/A-Life/e_aminoscience/bc/amino_16.html, one page.
Adams, Dr. Clifford A., "What are Nutricines?", www.eclecticcooking.com/WhatAreNutricines.htm, pp. 1-2.
Lardy, Greg, Poland, Chip, "Feeding Management for Horse Owners", AS-953, www.ext.nodak.edu/extpubs/ansci/horse/as953w.htm, Feb. 2001, pp. 1-6.
"Mycosorb", translate.google.com/translate?hl=en&sl=pt&u=http:/www.va-industria.pt/support.html&prev=/search%3Fq%3Dmycosorb%26hl%3Den%26, one page.
"Alltech to Exhibit Range of Natural Products at Space 2002", www.alltech-bio.com/alltech%5Calltech2.nsf/pages/News_Alltech_to_Exhibit_Range_of_Natural_Products_at_Space_2002, one page.
"Unraveling the Mystery of Mycotoxins", www.alltech-bio.com/alltech%5Calltech2.nsf/pages/News_UNRAVELLING_THE_MYSTERY_OF_MYCOTOXINS, one page.
"Consistent Responses Confirm Bio-Mos Efficacy", www.alltech-bio.com/alltech%5Calltech2.nsf/pages/News_CONSISTENT_RESPONSES_CONFIRM_BIO-MOS_EFFICACY, one page.
"L-Glutamine Side Effects and Benefits", www.bodybuildingforyou.com/supplements-reviews/glutamine-side-effects-benefits.htm, pp. 1-2.
Miller, Alan L. M.D., "Therapeutic Considerations of L-Glutamine: A Review of the Literature", pp. 1-11.
Reynolds, Judith A., Ph.D, P.A.S., "Are You Feeding Your Horse Like a Horse?", Moorman's Feed Facts, Oct. 2000, pp. 1-4.
Winawer, Neil M.D.; Williams, Mark V., M.D.; Making Health Care Safer: A Critical Analysis of Patient Safety Practices; Chapter 33. University of California at San Francisco (UCSF)—Stanford University Evidence-based Practice Center, AHRQ Publication 01-E058. Jul. 20, 2001.
Bekers M et al. "Oats and fat-free milk based functional food product" Food Biotechnology, Dekker, New York, NY, US, 15(1), 1-12 (2001).
McClure SR, Glickman LT, Glickman NW. Prevalence of gastric ulcers in show horses. J Am Vet Med Assoc 1999;215: 1130-1 133.
Traub-Dargatz JL, Kopral CA, Seitzinger AH, Garber LP, Forde K, White NA. Estimate of the national incidence of and operation-level risk factors for colic among horses in the United States, spring 1998 to spring 1999. J Am Vet Med Assoc. Jul. 1, 2001;219(1):67-71.

Lorenzo-Figueras M, Merritt AM. Effects of exercise on gastric volume and pH in the proximal portion of the stomach of horses. An J Vet Res. 2002;63:1481-1487.

Mair, Tim, Tom Divers, and Norm Ducharme. Manual of Equine Gastroenterology. London: WB Saunders, 2002.

Mitchell RD. Prevalence of Gastric Ulcers in Hunter/Jumper and Dressage Horses Evaluated for Poor Performance. Assoc. Equine Sports Med., Sep. 2001.

Kronfeld DS. Speed Limit. Dipl. ACVN, Dipl. ACVIM. Mar. 2003 Article # 4212.

Pellegrini, Frank. A Large-scale Necroscopy of Equine Ulcers. Submitted to Equine Veterinary Journal, 2004.

Martin GP, Marriott C, Kellaway IW. The interaction of progesterone with mucus glycoproteins. Pharm Acta Helv. 1981;56(1):5-8.

Kiviluoto T, Paimela H, Mustonen H, Kivilaakso E. Exogenous surface-active Phospholipids protects Necturas gastric mucosa against luminal acid and barrier-breaking agents. Gastroenterology. Jan. 1991; 100(1):38-46.

McNeil PL, Ito S. Gastrointestinal cell plasma membrane wounding and resealing in vivo. Gastroenterology. May 1989; 96(5 Pt 1): 1238-48.

Dupree JL, Coetzee T, Blight A, Suzuki K, Popko B (1998), Myelin galactolipids are essential for proper node of Ranvier formation in the CNS. J Neurosci 18(5):1642-49.

Kreitler B. Feed and Nutrition: Fat: The Next Nutraceutical? Thoroughbred Times, Apr. 12, 2003.

Davidson MH, Dugan LD, Burns JH, et al. The hypocholesterolemic effects of betaglucan in oatmeal and oat bran. A dose-controlled study. JAMA 1991;265:1833-9.

Bell S, Goldman VM, Bistrian BR, et al. Effect of beta-glucan from oats and yeast on serum lipids. Crit Rev Food Sci Nutr 1999;39:189-202 [review].

Braaten JT, Scott FW, Wood PJ, et al. High beta-glucan oat bran and oat gum reduce postprandial blood glucose and insulin in subjects with and without type 2 diabetes. Diabet Med 1994; 11:312-8.

Tappy LE, Gugolz E, et al. Effects of breakfast cereals containing various amounts of beta-glucan fibers on plasma glucose and insulin responses in NIDDM subjects. Diabetes Care 19(8):831-4, Aug. 1996.

Czop JK. The role of beta-glucan receptors on blood and tissue leukocytes in phagocytosis and metabolic activation. Pathol Immunopahtol Res 1985;5:286-96, 1986.

Estrada A, Yun CH, Van Kessel A, et al. Immunomodulatory activities of oat beta-glucan in vitro and in vivo. Microbiol Immunol 1997;41:99 1-8.

Reid DM, Montoya M, et al. Expression of the beta-glucan receptor; Dectin-1, on murine leukocytes in situ correlates with its function in pathogen recognition and reveals potential roles in leukocyte interactions. J Leukoc Biol 76(1):86-94, Jul. 2004.

Bolm N, Kulicke W. Rlzeological studies of barley (1-3)(1-4) beta-glucan in Concentrated solution, Carbohydrate Research, 1999, 315, 293-301.

Wursch P, Sunyer FX. The role of viscous soluble fiber in the metabolic control of diabetes. A review with special emphasis on cereals rich in beta-glucan. Diabetes Care 20(11):1774-80, 1997.

Roth E, Spittler A, Oehler. Glutamine: effects on the immune system, protein balance and intestinal functions. Wien Klin Wochenshr. 1996;108(21):667-8.

Duckworth DH, Madison JB, et al. Arteriovenous differences for glutamine in the equine gastrointestinal tract. Am J Vet Res 53(10):1864-7, Oct. 1992.

Vazquez P, Gomez de Segura IA, Cos A, Candela CG, De Miguel E. Response of the intestinal mucosa to different enteral diets in situations of surgical stress and malnutrition. Nutr Hosp. Nov.-Dec. 1996; 11(6):321-7.

Bertolo RF, Chen CZ, Law G, Pencharz PB, Ball RO. Threonine requirement of neonatal piglets receiving total parenteral nutrition is considerably lower than that of piglets receiving an identical diet intragastrically. J Nutr. Oct. 1998; 128(10):1752-9.

Ball RO, Law G, Bertolo RFP, Pencharz PB. Adequate oral threonine is critical for mucin production and mucosal growth by neonatal piglet gut. Proceedings of the VIIIth International Symposium on Protein Metabolism and Nutrition, EAAP, 1999.

Cuaron JA, Chapple RP, Easter RA. Effect of lysine and threonine supplementation of Sorghum in gestation diets on nitrogen balance and plasma constituents in first litter gilts. J. Anim. Sci., 58, 631-637, Mar. 1984.

Bueno J, Torres A, Almendros A, Carmona R, Nunez MC and Gil A, (1994) Effect of dietary nucleotides on small intestinal repair after diarrhea. Histological and ultrastructural changes. Gut 35:926-933.

Uauy R, Stringel G, Thomas R and Quan R, (1990) Effect of dietary nucleosides on growth and maturation of the developing gut in the rat. J. Pediatr. Gastroenteral. Nutr. 10:497-503.

Marshman E., Booth C., Potten CS., The intestinal epithelial stem cell. Bioessays Jan. 2002; 24(1):91-8.

Lin, Cheng-mao. Effect of Dietary Nucleotide Supplementation on in Vivo and in Vitro Immune Function in Protein-Malnourished Mice. University of Florida. PhD. Dissertation. Dec. 1995.

Ip WK, Lau YL. Role of mannose-binding lectin in the innate defense against *Candida albicans*: enhancement of complement activation, but lack of opsonic function, in phagocytosis by human dendritic cells. J Infect Dis Aug. 1, 2004;190(3):632-40. Epub Jun. 28, 2004.

Swanson KS, Grieshop CM, Flickinger EA, Healy HP, Dawson KA, Merchen NR, Fahey GC Jr. Effects of supplemental fructooligosaccharides plus mannanoligosaccharides on immune function and ileal and fecal microbial populations in adult dogs. Arch Tierenahr. Aug. 2002;56(4):309-18.

Bland EJ, Keshavarz T, Buclte C. The influence of small oligosaccharides on the immune system. Carbohydrate Research, vol. 339, issue 10, 2004.

Newman, K. 1994. Mannan-oligosaccharides: Natural polymers with significant impact on the gastrointestinal microflora and the immune system. Biotechnology in the Feed Industry, Nottingham University Press, Nottingham, UK, pp. 167-174.

Davis E., Maxwell C., Kegley B., de Rodas B., Friesen K and Hellwig D., Efficacy of Mannan Oligosaccharide (Bio-Mos) Addition at Two Levels of Supplemental Copper on Performance and Immunocompetence of Early Weaned Pigs. Arkansas Animal Science Department Report 1999.

* cited by examiner

FIG.

DIETARY SUPPLEMENT AND METHOD FOR THE TREATMENT OF DIGESTIVE TRACT ULCERS IN EQUINES

BACKGROUND OF THE INVENTION

Field of the Invention

The present invention relates generally to feed supplements and to the treatment of ulcers in horses and other animals, and more particularly to a novel feed supplement and nutritional aid for the efficacious treatment and/or inhibition of digestive tract ulcers in horses and other animals.

The incidence of digestive tract ulcers in performance horses has risen most sharply, from approximately twenty percent in 1920 to approximately ninety percent or better in the last decade. In racehorses, for example, as much as ninety-seven percent of the racehorse population has been reported to have digestive tract ulcers, with the percentage of show horses having digestive tract ulcers lagging only slightly behind. Even performance horse foals have been inflicted with this condition, with approximately sixty percent of performance horse foals having digestive tract ulcers. While pleasure horses have a lower incidence of digestive tract ulcers than show horses, the increasing incidence of digestive tract ulcers in the last two decades has been significant for all segments of the horse population, including pleasure horses.

A recent scientific study of a random cross-section of horses indicated that approximately fifty-five percent of them had gastric ulcers and forty percent of them had colonic ulcers. The incidences of gastric and colonic ulcers were not identical, meaning that some horses had only gastric ulcers and other horses had only colonic ulcers. However, a large percentage of the horses that had colonic ulcers also had gastric ulcers, with less than thirty percent of the horse population as a whole not having either gastric or colonic ulcers. As mentioned above, the incidence of digestive tract ulcers for show horses and racehorses is even higher than these statistics for the general horse population.

The direct cause of digestive tract ulcers in horses appears to be excess stomach acid, as is the case with humans and other animals. Excess stomach acid can "eat" through the protective lining of the stomach and damage the interior surface of the stomach, causing gastric ulcers. In humans, it is believed that the prevalent factor in the development of stomach ulcers is the helicobacter pylori bacteria. However, the helicobacter pylori bacteria has not been isolated from horse stomachs, and thus is not believed to be a factor in the development of digestive tract ulcers in horses.

One factor contributing to the high incidence of digestive tract ulcers in horses is the somewhat unique digestive tract anatomy of horses. While horses are monogastric (one stomach) animals, they are also hindgut fermenters, which means that they have relatively small stomachs and small intestines (collectively referred to as the foregut), and relatively large colons (collectively referred to as the hindgut). The relative volume of the foregut in horses is approximately thirty-five to forty percent of the total volume of the digestive tract. By comparison, the relative volume of the foregut in pigs is sixty to sixty-five percent of the total volume of the digestive tract, and the relative volume of the foregut in ruminant animals such as cows is eighty-five to ninety percent of the total volume of the digestive tract.

While the foregut of horses is relatively small, their stomachs are even smaller, representing only approximately one-quarter of the volume of the foregut, and thus approximately nine percent of the total volume of the digestive tract. In view of the small percentage of the digestive tract represented by the stomach, one might refer to a horse's stomach as a preparatory chamber. The principal consequence of this relatively small stomach size is that the rate of passage of feed through horses' stomachs is relatively fast, leaving relatively little time for the digestion process to occur. In addition, smaller feed particles pass through horses' foreguts even more quickly, with the time of passage of such smaller particles through the horses' stomachs potentially not allowing for proper digestion to occur.

In the case of humans and most other animals, gastric acid is secreted in the stomach in response to eating. In contrast, horses have developed over millennia as trickle feeders (eating slowly but more or less continuously over most of the day), and their digestive systems are geared for such a diet, with a continuous production of gastric juices and bile secretion into the foregut from the liver. Thus, the stomach of a horse may be thought of as an acid pump that produces gastric acid more or less continuously through the day, whether or not the horse is being fed.

The inside wall of the stomach is protected by a mucous gut membrane lining which is a fatty layer containing polar lipids. When there is no food contained in the horse's stomach, the gastric acid will act on the mucous gut membrane lining the inside wall of the stomach, oxidizing the cells of the gut lining and burning them up. These burned-up gut lining cells are sloughed off, and pass through the digestive system, exposing the gut wall to the gastric acid and allowing gastric ulcers to form. This condition is known as equine gastric ulcer syndrome ("EGUS").

In addition, there is a continuous peroxidation and oxidation of proteins and lipids which results in the formation of free radicals. As the fatty cells containing polar lipids in the mucous gut membrane are oxidized and burned off, free radicals are created. These free radicals can break down muscle tissue, and have been shown to have an adverse affect on the performance of horses. Thus, it is readily apparent to those skilled in the art that digestive tract ulcers have a substantial adverse effect on performance horses, and can prevent performance horses from achieving their true potential.

In the case of humans, the production of saliva and its mixing with ingested foodstuffs initiates the digestion process since human saliva includes the enzyme amylase, which breaks down starch into sugar. Horse saliva does not contain amylase or any other enzyme that can initiate the digestion process. However, horse saliva does contain a buffering agent that can help to neutralize gastric acid contained in the horse's stomach.

Another unique feature of horses' digestive tracts is the presence of a large microbial population in the hindgut. These microorganisms are responsible for the fermentation of the residues of the digestive process and absorption of digested feed, and have the ability to utilize the cellulose that is present in forages. The anatomy of the hindgut, which has a number of folds contained therein, causes the passage of ingested feed to pass through relatively slowly as compared to the rate of passage of ingested feed through the foregut. While this is advantageous when digesting roughages such as forage, it can also predispose a horse to digestive upsets when insufficient roughage is contained in the ingested feed.

In addition to the unique anatomy of horses' digestive tracts, there are several other factors which also appear to increase the incidence of digestive tract ulcers in horses. These factors include feeding practices, physical stress (including the stress from being in a stable as much as twenty-three hours of the day), and medications being given to the horses. In the case of performance horses, two additional factors which can also increase the incidence of digestive tract ulcers are the intensity of training and the initiation of training of foals at a young age, the latter of which is particularly prevalent with racehorses. However, it has been determined by the inventors that while all of these factors are significant, the primary factors are the unique physiology of the horse digestive tract and modern feeding practices, with the other factors acting to further exacerbate a condition which is essentially caused by two aforesaid primary factors.

Thus, other than the unique physiology of horses' digestive tracts, the primary factor leading to the high incidence of digestive tract ulcers in horses is diet-related, and is a consequence of a drastic change in the diet of most horses. Until the relatively recent past, horses for the most part had been allowed to be free-range grazers, with a diet that consisted primarily of forage. However, beginning in the 1920's, fewer and fewer horses have had the opportunity to free range graze, or even to have the freedom to eat hay or other forage during much of the day. Instead, most horses are fed diets that are high in grains, with forage either being reduced to minimal levels or eliminated entirely from the horses' diets. Typical feeding schedules for horses are twice or three times daily, generally with feedings in the morning and the evening, and a third feeding at midday, mimicking a human diet. With this change in diet, the incidence of digestive tract ulcers in horses has increased tremendously, especially in performance horses (including both racehorses and show horses), which also have additional stresses that exacerbate the problem caused by the consequences of a low forage diet and the nature of the digestive tract of horses.

When horses are allowed to eat forage (which is essentially high fiber, low nutrition material), as they have evolved to do, they typically eat for approximately sixteen hours a day. If allowed to graze, they will begin feeding in the early morning, and will continue to feed until well after dark, nibbling, chewing, swallowing, and digesting slowly to keep their small stomachs from becoming empty. Given free choice, horses will search out and find a balanced diet typically consisting of grasses, berries, and leaves, which provide a balance of essential microminerals in addition to basic volume and energy requirements. The constant chewing produces saliva that neutralizes the gastric acid. (Saliva contains positive ions ("cations") which counteract the negative ions ("anions") of gastric acid.)

Most horses today are neither kept in pastures where they can eat forage all day long, nor fed forage in a stable. Instead, stabled horses are typically fed a concentrated, low volume diet of grain products with relatively small quantities of hay or forage being available to them, and then only intermittently. With regard to racehorses and other performance horses, the diet bears even less resemblance to a forage diet. Racehorses are fed a high-energy diet to maximize muscle growth and activity levels; this diet typically consists of a mixture of grains, molasses, nutrients, and feed additives, usually with minimal hay in the form of one or two flakes with each meal.

The concentrated, low volume diet of grain products is generally fed to the horses three times (or in some cases only twice) a day, and the horses generally eat it rapidly. When fed to horses, such a low volume diet of grain products passes through their stomachs relatively quickly. Since this type of diet is concentrated and of high quality, horses fed such a diet are not nutritionally underfed; rather, they are "behaviorally" underfed. Diets that are low in fiber and high in starch increase the potential that starches which are not digested in the foregut will enter the hindgut, where they will rapidly ferment, causing a rapid reduction in the pH level in the hindgut and a volatile fatty acid imbalance. The acidic environment created in this manner has a direct effect on the balance of microflora (the huge community of microorganisms which forms a complex and dynamic ecosystem within the hindgut) within the hindgut.

One consequence of such a diet is that relatively little of the buffering saliva reaches the horses' stomachs. This is due to the fact that the buffering capacity is determined mainly by the volume of saliva that is produced while horses are eating. For a given weight of concentrated food such as grain products, the volume of saliva produced is less than half the volume of saliva that would be produced by the same weight of forage. Thus, it will at once be appreciated by those skilled in the art that, except for the relatively brief time when horses are eating and shortly thereafter, their stomachs will be empty, with no buffering saliva. Since horses' stomachs are not adapted to such intermittent feeding, they will constantly be bathed with gastric acid, causing gastric ulcers.

Since the gastric acid from the stomach can flow into the hindgut, it is also possible for horses to have colonic ulcers, particularly ulcers in the large intestine, typically in the right ventral colon. The consequences of colonic ulcers in horses are caused or exacerbated due to the presence of pathogens and mycotoxins in the hindgut. These pathogens and mycotoxins can fasten themselves onto the lesions and cause infections in the walls of the hindgut. The pathogens and mycotoxins are ingested by horses in their feed, and are metabolites of funguses growing on the feed. Generally, the pathogens and mycotoxins will pass through horses' digestive tracts unless there are colonic ulcers that are susceptible to the pathogens and mycotoxins. Pathogens and mycotoxins can cause severe problems including digestive, reproductive, neurological, and athletic problems, as well as chronic obstructive pulmonary disease ("COPD") in horses. For example, colonization on sites of colonic ulcers caused by pH changes and attack by acids can cause transit of mycotoxins into the blood, and eventually may result in damage to the liver and even renal dysfunctions.

There are three solutions to the problem of digestive tract ulcers in horses that have been utilized in the art, none of which have been satisfactory. The first known solution is the use of antacids, also referred to euphemistically as "gastric ulcer transnutrients." Antacids (typically mixtures of magnesium and aluminum hydroxide) are administered to temporarily neutralize acid in the stomach. However, antacids are treating the symptom rather than the problem, and are relatively ineffective due to the fact that they pass rapidly through horses' stomachs, and thus an increase in pH in the stomach that is achieved with antacids is typically of short duration. In addition, since gastric acid is constantly produced by horses, it will at once be appreciated by those skilled in the art that antacids are substantially ineffective in treating digestive tract ulcers in horses.

The second known solution is the use of drugs, which are administered to inhibit the production of gastric acid. These are presently three classes of drugs which are used for this purpose: histamine type-2 antagonists such as cimetidine (available from GlaxoSmithKline under its registered trademark Tagamet) and ranitidine (available from Pfizer under its registered trademark Zantac or from Ranvet under its registered trademark Ulcerguard), or proton pump inhibitors such as omeprazole (available from Astra AB under its registered trademark Gastrogard). These drugs claim to be effective in curing gastric ulcers in three to four weeks, but are very expensive. It is apparent to those skilled in the art that the temporary change in the stomach environment is highly unlikely to result in complete restoration of health during treatment.

They do have several disadvantages in addition to their expense, the most problematic of which is that once they are discontinued the digestive tract ulcers will usually recur quickly, requiring another round of treatment. In some instances, veterinarians may find it necessary to prescribe continuing treatment with one of these medications, which becomes extremely expensive. In addition, some of these drugs must be withheld prior to racing in the case of racehorses. Another profound disadvantage is that these drugs interfere with proper digestion by changing the natural pH balance, which results in the treated horses being in less than optimum condition.

The third, and most effective, known solution is the only natural solution known at present—rest and a diet of forage. This means allowing horses to return to pasture, and a diet of hay and other forage. It is the only real solution that has been known in the art, and it is the universal prescription to provide a complete return to health. For performance horses, it may inhibit the ability of the horses to compete; for owners of other horses it represents an ideal solution that is simply not possible. Accordingly, rest and diet does not represent an optimal solution for many horses and their owners.

It is accordingly the primary objective of the dietary supplement of the present invention that it efficaciously treat digestive tract ulcers in horses and, potentially, in other animals and even humans as well. In addition to having the effect of efficaciously treating digestive tract ulcers, it is a related objective of the dietary supplement of the present invention that it demonstrate efficacy in the prevention of such digestive tract ulcers as well. It is a further objective of the dietary supplement of the present invention that it be effective in treating and/or preventing gastric ulcers, and it is a related objective of the preferred embodiment of the dietary supplement of the present invention that it also be effective in treating colonic ulcers as well.

It is another objective of the dietary supplement of the present invention that it not interfere with the proper digestion of foodstuffs while it is treating and/or preventing digestive tract ulcers. It is an additional objective of the dietary supplement of the present invention that it consist entirely of safe and natural ingredients rather than drugs. It is a still further objective of the dietary supplement of the present invention that it be orally administrable, thereby making its dispensation a simple matter. It is a related objective of the dietary supplement of the present invention that it be packaged in single doses to make its administration as convenient as is possible.

The dietary supplement of the present invention must also be both stable and have a commercially acceptable shelf life, and it should also require no special care to be provided by the user throughout its shelf life prior to usage. In order to enhance the market appeal of the dietary supplement of the present invention, it should also be relatively inexpensive when compared to previously known methods of digestive tract ulcer treatment to thereby afford it the broadest possible market. Finally, it is also an objective that all of the aforesaid advantages and objectives of the dietary supplement of the present invention and its method of administration be achieved without incurring any substantial relative disadvantage.

SUMMARY OF THE INVENTION

The disadvantages and limitations of the background art discussed above are overcome by the present invention. With this invention, a novel dietary supplement that is specifically formulated to treat and/or prevent digestive tract ulcers is provided. Through the periodic administration of this dietary supplement to horses or other animals in accordance with methods taught by the present invention, digestive tract ulcers are effectively treated and/or prevented in such horses or other animals. As will rapidly become apparent to those skilled in the art, the dietary supplement of the present invention is much more than the sum of its ingredients, with the combination of ingredients yielding a synergistic result substantially more efficacious than the results which would be produced if each of the ingredients acting by itself were provided to horses or other animals.

In its basic form, the dietary supplement of the present invention is targeted to accomplish three goals, each of which is facilitated by the inclusion of a particular ingredient or a mixture of ingredients in the dietary supplement. The first goal is to strengthen the mucous gut membrane lining the inside wall of the stomach, to help the mucous gut membrane retain its ability to protect the inside wall of the stomach. This involves enhancing the cationic efficiency of the mucous gut membrane, by producing additional cations, or positive ions, to counteract the anions, or negative ions, in the gastric acid.

The ingredient of the dietary supplement of the present invention which strengthens the mucous gut membrane lining the inside wall of the stomach is a polar lipid supplement. In the preferred embodiment, the polar lipid supplement is oat oil, which contains a high concentration of polar lipids and antioxidants. Optionally, different phases of oat oils may be used in order to vary the viscosity of the oat oil, which may be advantageous depending upon the intended method of administration of the dietary supplement of the present invention. For example, if the dietary supplement is to be administered orally by syringe, a more viscous oat oil mixture would be used than if the dietary supplement were to be administered by pouring it onto feed that is then ingested.

The second goal of the dietary supplement of the present invention is to slow the passage of feed ingested together with or in close proximity to administration of the dietary supplement through the stomach, which in and of itself will be highly beneficial. In conjunction with this second goal, it is also the most readily apparent benefit of slower transit of feed through the stomach is that during the increased time that feed spends in the stomach, gastric acid will not be attacking the mucous gut lining the inside wall of the stomach. In addition, by causing feed to spend a greater amount of time in the stomach, the digestion of the feed will be improved, also benefiting the health of horses.

The ingredient of the dietary supplement of the present invention which slows the transit of feed through the stomach is a soluble fiber. In the preferred embodiment, β-glucan (beta-glucan), which is the soluble fiber in oats, is used as this ingredient. β-glucan is an oligosaccharide that is found in the kernel of oats, and is a powder when dried. It is a jelling agent that has an increased jelling effect when exposed to water, and also has a beneficial spreading effect that spreads the dietary supplement on the inner surface of the stomach.

The third goal of the dietary supplement of the present invention is to increase the integrity of the mucous gut membrane lining the inside wall of the stomach. The way in which the dietary supplement accomplishes this goal is by increasing the rate of cell growth in the mucous gut membrane. By increasing the rate of cell growth in the mucous gut membrane lining the inside wall of the stomach, the dietary supplement of the present invention can effectively strengthen the mucous gut membrane and thereby enable it to continue to protect the inside wall of the stomach.

The ingredient of the dietary supplement of the present invention which increases the integrity of the mucous gut membrane lining the inside wall of the stomach is one or more nutricines such as surfactant amino acids. In the preferred embodiment, L-threonine and/or L-glutamine are used as this ingredient. Both L-threonine and L-glutamine are naturally produced amino acids that are produced by breaking down a protein.

It will be appreciated by those skilled in the art that these three ingredients of the dietary supplement of the present invention represent a balanced, multifaceted solution to the problem posed by gastric ulcers in horses. With this solution, the dietary supplement protects the stomach wall from gastric acid in three ways: by providing polar lipids to strengthen the mucous gut membrane and increase the cationic efficiency of the mucous gut membrane; by increasing the amount of time feed is in the stomach, thereby reducing the amount of time that the stomach is empty and exposed to gastric acid; and by increasing the integrity of the mucous gut membrane. It is believed that the dietary supplement of the present invention would also have efficacious application to other animals, including humans.

In the preferred embodiment, the dietary supplement of the present invention also includes one or more ingredients to absorb and eliminate mycotoxins and/or pathogens (i.e., bacteria) in the hindgut (the intestines and the colon), thereby treating and/or preventing colonic ulcers. One such ingredient that can be used is a mycotoxin absorbant material that absorbs or soaks up mycotoxins in the hindgut. Another such ingredient that can be used is a pathogenic bacteria absorbant material that attracts bacteria and passes through the digestive system in the feces.

The ingredients of the dietary supplement of the present invention which absorb or soak up mycotoxins and/or attract and eliminate pathogens are nutricines which may be made from saccharomyces cerevisiae (brewer's yeast). In the preferred embodiment, a mycotoxin absorbant such as the material marketed under the registered trademark MYCOSORB by Alltech, Inc., may be used to absorb or soak up mycotoxins in the colon. Additionally, in the preferred embodiment, a pathogenic bacteria absorbant such as the material marketed under the trademark BIOMOS by Alltech, Inc., may be used to attract and eliminate pathogens.

Finally, in the preferred embodiment, the dietary supplement of the present invention also includes an ingredient to keep the dietary supplement at a neutral pH. Typically, when the above-described ingredients are mixed together to make the dietary supplement of the present invention, the mixture will have an acidic pH. Accordingly, a material that can be used to keep the dietary supplement at a neutral pH is sodium bicarbonate.

The dietary supplement of the present invention can be administered in any of a number of ways, and may either be added to feed or fed directly as a dietary supplement. It is desirable that the animal is given a regular dose of the dietary supplement, which in the preferred embodiment is daily in order to maintain an optimal level of the ingredients in the animal's digestive tract. The dietary supplement of the present invention may be manufactured as a liquid, in which case it can be added to feed which is then fed to a horse. Alternately, it may be manufactured as a liquid or paste and stored in a gelatin capsule (as gelcaps), which makes for a consistent dosage of the dietary supplement. Finally, it can be manufactured as a paste for oral administration using a dose syringe. In practice, even when giving horses the dietary supplement at times other that their normal feeding, they see it as a treat since they like its taste.

Upon disclosure of the dietary supplement of the present invention to those skilled in the art, they will immediately appreciate that the dietary supplement is much more than merely the sum of its ingredients. The combination of polar lipid supplement, soluble fiber, and nutricines yield a synergistic result substantially more efficacious than a sum of the results which would be produced if each ingredient by itself was used. In addition to the utility of the polar lipid supplement to strengthen the mucous gut membrane lining the inside wall of the stomach, the polar lipid supplement also acts as a spreading agent which enhances the efficacy of the soluble fiber and the nutricines by spreading them to cover the entire digestive tract. The soluble fiber slows down the passage of the polar lipid supplement and the nutricines, giving them more time to provide their beneficial effects on the digestive tract. The nutricines also increase the integrity of the gut membrane, but are much more effective with the polar lipid supplement than they would be without it.

It may therefore be seen that the present invention teaches a dietary supplement which efficaciously treats digestive tract ulcers in horses and, potentially, in other animals and even humans as well. The dietary supplement of the present invention can be fed to any animal including, but not limited to, avian, bovine, porcine, equine, ovine, caprine, canine, and feline species. In addition to having the effect of efficaciously treating digestive tract ulcers, the dietary supplement of the present invention demonstrates efficacy in the prevention of such digestive tract ulcers as well. The dietary supplement of the present invention is effective in treating and/or preventing gastric ulcers, and in treating colonic ulcers as well.

The dietary supplement of the present invention does not interfere with the proper digestion of foodstuffs while it is treating and/or preventing digestive tract ulcers. It consists entirely of safe and natural ingredients rather than drugs. The dietary supplement of the present invention is orally administrable, thereby making its dispensation a simple matter. It can also be packaged in single doses to make its administration as convenient as is possible.

The dietary supplement of the present invention is stable and has a long shelf life, and requires no special care to be provided by the user throughout its shelf life prior to usage. The dietary supplement of the present invention is also inexpensive relative to previously known dietary tract ulcer treatments, thereby enhancing its market appeal and affording it the broadest possible market. Finally, all of the aforesaid advantages and objectives of the dietary supplement of the present invention and its method of administration are achieved without incurring any substantial relative disadvantage.

DESCRIPTION OF THE DRAWINGS

These and other advantages of the present invention are best understood with reference to the drawings, in which.

DETAILED DESCRIPTION OF THE PREFERRED EMBODIMENT

Figure 1:
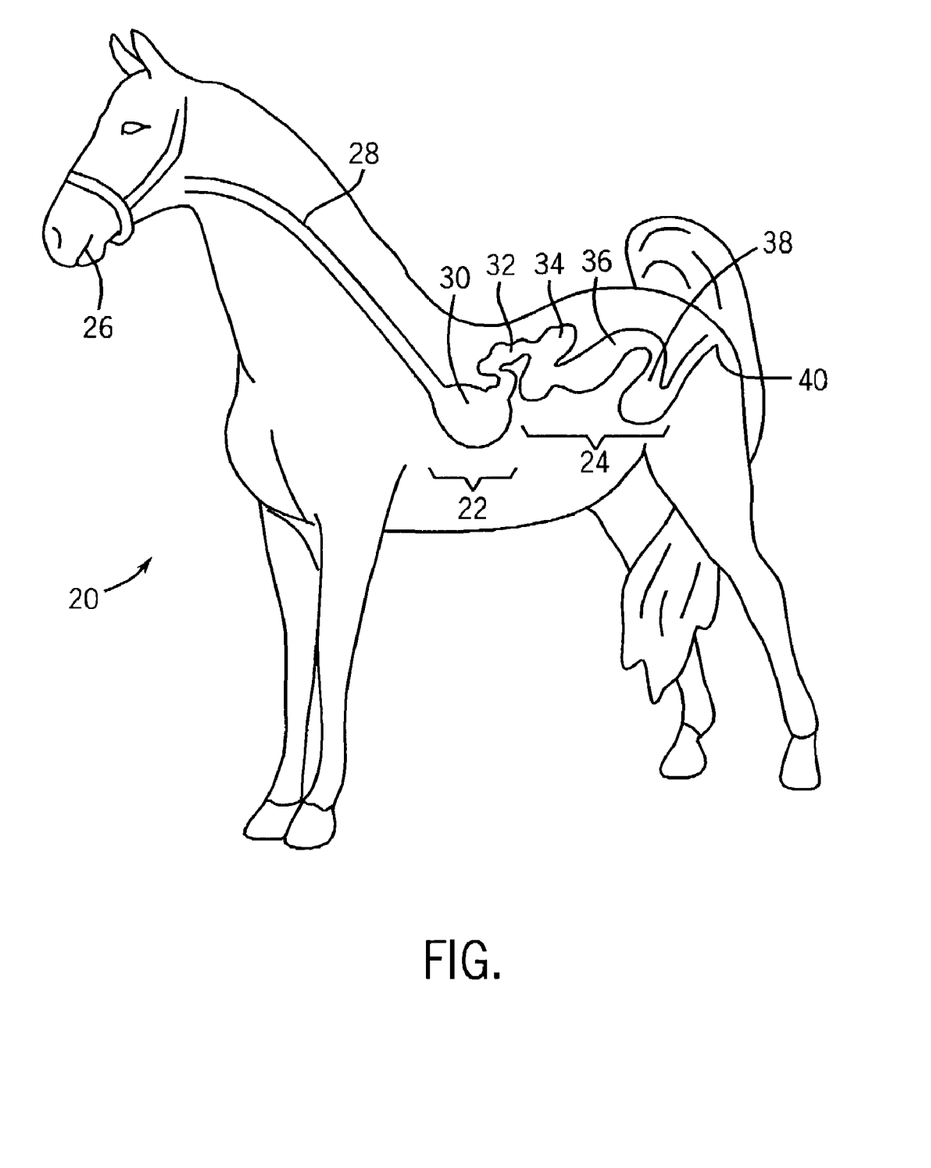
FIG. 1 is a somewhat schematic drawing of a horse showing the anatomy of the horse's digestive tract.

Prior to a discussion of the dietary supplement of the present invention and methods of making and administering it, it is helpful to briefly discuss the anatomy of the digestive system of a horse. Referring to the FIGURE, a side view of a horse 20 is illustrated, schematically illustrating the digestive tract of the horse. The digestive tract of the horse 20 may be separated into a foregut, which is indicated generally by the reference numeral 22, and a hindgut, which is indicated generally by the reference numeral 24.

The digestive tract of the horse 20 begins at its mouth 26, and sequentially extends through an esophagus 28 into a stomach 30 and then into a small intestine 32, which together constitute the foregut 22 of the horse 20. The foregut 22 of the horse 20 constitutes approximately thirty-five to forty percent of the relative capacity of the digestive tract of the horse 20.

From the small intestine 32, the digestive tract extends through a cecum 34, a large colon 36, and a small colon 38 which terminates in a rectum 40. These elements of the digestive tract of the horse 20 together constitute the hindgut 24 of the horse 20. The hindgut 24 constitutes approximately sixty to sixty-five percent of the relative capacity of the digestive tract of the horse 20.

In its simplest implementation, the preferred embodiment of the dietary supplement of the present invention includes three primary ingredients which are mixed together to manufacture the dietary supplement. These ingredients are a polar lipid supplement to strengthen the mucous gut membrane lining the inside wall of the stomach, a soluble fiber to slow the transit of feed through the stomach, and one or more nutricines such as surfactant amino acids which increase the integrity of the mucous gut membrane. Each of these ingredients will be discussed separately below, together with a description of its preferred composition, alternative compositions, the preferred amount of the composition used in the dietary supplement, and the range of the amount of the composition which may be used in the dietary supplement. During the following discussion of the ingredients of the dietary supplement of the present invention, it will rapidly become apparent to those skilled in the art that the benefits achieved by the dietary supplement of the present invention are substantially greater than the sum of the individual benefits of each of the dietary supplement's ingredients.

The first primary ingredient of the dietary supplement of the present invention is a polar lipid supplement to strengthen the mucous gut membrane lining the inside wall of the stomach. Anions, or negative ions, in the gastric acid in the stomach cause a loss of integrity in the cell walls of the mucous gut membrane that protects the inside wall of the stomach. There is an accompanying loss of polar lipids within the cells of the mucous gut membrane, and an increase in free radicals. Membrane synthesis occurs mainly through the addition of new polar lipids to the cells. Polar lipids from the dietary supplement accordingly replace the polar lipids lost due to the gastric acid, and enhance the cationic efficiency of the mucous gut membrane by producing additional cations, or positive ions, to counteract the anions in the gastric acid.

There are a number of potential sources of polar lipids that may be used as the polar lipid supplement in the dietary supplement of the present invention. In the preferred embodiment, oat oil is used due to the fact that oat oil has more polar lipids per unit volume than any other any other polar lipid source. Oat oil is also an excellent source of antioxidants. Other oils that are also good sources of polar lipids are soybean oil, olive oil, palm oil, sunflower oil, corn oil, rapeseed oil, linseed oil, etc.

In the preferred embodiment of the dietary supplement of the present invention, the polar lipid supplement is made of different viscosity components of oat oil (or other polar lipid ingredients) in order to affect the ultimate character of the dietary supplement. Like most oils, oat oil may come from multiple extractions, with the typical extraction process crushing the oats and treating them with an extraction agent such as hexanol. The first phase of oat oil extracted is a thin oil. The second phase of oat oil extracted is a thick oil, which is considerably more viscous than the first phase. The third phase of oat oil extracted is a very thick oil that has the consistency of grease. All three phases of the oat oil extraction process may be mixed, with the resulting mixture being referred to herein as oat oil. Optionally, the third phase of oat oil can be mixed with the oat oil consisting of all three phases to further thicken it. While there are a variety of sources for oat oil, a commercial source for the third phase of oat oil is Swedish Oat Fiber AB in Gothenburg, Sweden, which manufactures such a product under the trademark "Avenol."

The second primary ingredient of the dietary supplement of the present invention is a soluble fiber to slow the transit of feed through the stomach. With foodstuffs contained in the stomach for a longer period of time, gastric acid will have proportionately less time to attack the mucous gut lining protecting the inside wall of the stomach. Also, by slowing the transit of ingested foodstuffs through the stomach, digestion of the foodstuffs in the stomach will be substantially enhanced. This results in proportionately less digestion occurring in the hindgut, minimizing the rapid fermentation phenomenon which causes a rapid reduction in the pH level in the hindgut and a volatile fatty acid imbalance.

There are a number of potential sources of soluble fiber that may be used in the dietary supplement in the dietary supplement of the present invention. In the preferred embodiment, the soluble fiber used is β-glucan (beta-glucan) that is derived from oats. β-glucan is a jelling agent that has an increased jelling effect when water is ingested together with or shortly after the β-glucan itself is ingested. β-glucan also has a beneficial spreading effect that spreads the dietary supplement on the inner surface of the stomach. Other soluble fibers that are also good sources of β-glucan are those derived from barley or soybeans. β-glucan is widely available from a large number of different suppliers, and is a powder when dried.

The third primary ingredient of the dietary supplement of the present invention is one or more nutricines such as surfactant amino acids which increase the integrity of the mucous gut membrane. The nutricine(s) accomplish this by increasing the rate of growth of cells in the mucous gut membrane. Increasing the growth rate of these cells increases the viability of the mucous gut membrane in its corrosive environment of gastric acid, and better enables the mucous gut membrane to continue to protect the inside wall of the stomach.

There are a number of potential sources of nutricines that may be used in the dietary supplement. In the preferred embodiment, the nutricines are amino acid-based, and include both L-threonine and L-glutamine, which are both naturally produced amino acids which are produced by breaking down a protein. L-threonine makes up collagen, elastin, and enamel protein, assists in metabolism and assimilation, and aids the digestive system by increasing the integrity of the mucous gut membrane. L-threonine has also been observed by the inventors to have a synergistic effect with β-glucan in further slowing motility through the stomach.

L-glutamine is the most abundant amino acid in the bloodstream, and is primarily formed and stored in skeletal muscle and the lungs (and thus is not normally present in the stomach). L-glutamine also increases growth hormones, and when ingested has a substantial effect on maintaining and increasing mucosal integrity, including enhancing the integrity of the mucous gut membrane. Thus, L-threonine and L-glutamine both act to protect the inside wall of the stomach by enhancing the integrity of the mucous gut membrane. L-threonine and L-glutamine are widely available from a large number of different suppliers, and are also powders.

These three principal ingredients of the dietary supplement of the present invention thus protect the stomach wall from gastric acid in three ways which are enhanced by the interaction between the three ingredients: by providing polar lipids to strengthen the mucous gut membrane and increase the cationic efficiency of the mucous gut membrane; by increasing the amount of time feed is in the stomach, thereby reducing the amount of time that the stomach is empty and exposed to gastric acid; and by increasing the integrity of the mucous gut membrane. In the preferred embodiment, additional ingredients are included in the dietary supplement of the present invention to treat and/or prevent colonic ulcers.

The additional ingredient(s) of the dietary supplement of the present invention to treat and/or prevent colonic ulcers is one or more nutricines which are designed to absorb and eliminate mycotoxins and/or pathogens (i.e., bacteria) in the hindgut (the intestines and the colon). One of the additional ingredients used in the preferred embodiment is a mycotoxin absorbant nutricine that absorbs or soaks up mycotoxins in the hindgut. Another additional ingredient used in the preferred embodiment is a pathogenic bacteria absorbant material that attracts bacteria and passes through the digestive system together with the absorbed pathogenic bacteria in the feces.

In the preferred embodiment, the mycotoxin absorbant nutricine used to absorb or soak up mycotoxins in the hindgut is a mycotoxin absorbant material marketed under the registered trademark MYCOSORB by Alltech, Inc. Other mycotoxin absorbant nutricines that could instead be used include the material marketed under the trademark MYCOFIX PLUS by Biomin Distribution, Inc. and the material marketed under the trademark D-MYCOTOC by Kanzy Medipharm, Inc. In the preferred embodiment, the pathogenic bacteria absorbant material that attracts bacteria and passes through the digestive system together with the absorbed pathogenic bacteria is a pathogenic bacteria absorbant such as the material marketed under the trademark BIOMOS by Alltech, Inc. Other pathogenic bacteria absorbant nutricines that could instead be used include the material marketed under the trademark BIOSAF by S. I. Lesaffre, Cedex, France, as well as any mannanoligosaccharide (complex mannose sugars derived from the cell wall of yeast). MYCOSORB and BIOMOS are available from Alltech, Inc., in Nicholasville, Ky., and are also powders.

There is one additional ingredient that is included in the preferred embodiment in order to keep the dietary supplement at a neutral pH. When all of the previously mentioned ingredients of the dietary supplement of the present invention are mixed together, the resulting mixture will be have an acidic pH. Accordingly, an alkaline material is added to the dietary supplement to bring it to a neutral pH (typically a pH of approximately seven). In the preferred embodiment, that ingredient is sodium bicarbonate (also a powder). Alternately, other buffers could be used; for example, tris buffers or different aluminum salts that are used as antacids could be used instead of sodium bicarbonate.

Those skilled in the art will immediately appreciate that the dietary supplement of the present invention is much more than merely the sum of its ingredients, with the combination of ingredients yielding a synergistic and highly efficacious result. For example, the polar lipid supplement acts as a spreading agent that enhances the efficacy of the soluble fiber and the nutricines by spreading them to cover the entire digestive tract. The soluble fiber slows down the passage of the polar lipid supplement and the nutricines, giving them both more time to provide their beneficial effects on the digestive tract. The nutricines also increase the integrity of the gut membrane, but are much more effective in combination with the polar lipid supplement than they would be without it.

The relative ranges of amounts of each of the ingredients, and their preferred amounts, will now be discussed, beginning with the nutricines. First, the nutricines that increase the integrity of the mucous gut membrane, which in the preferred embodiment are L-threonine and L-glutamine, will be discussed. The range of amounts of L-threonine is between approximately one percent and eight percent of the dietary supplement by weight. The most preferred amount of L-threonine is approximately two and one-half percent of the dietary supplement by weight.

The range of amounts of L-glutamine is between approximately one percent and five percent of the dietary supplement by weight. It is believed that less than one percent of L-glutamine will result in little or no efficacious result. The most preferred amount of L-glutamine is approximately two percent of the dietary supplement by weight.

Next, the nutricines which absorb mycotoxins and bacteria in the hindgut, which in the preferred embodiment are BIOMOS and MYCOSORB, will be discussed. The range of amounts of BIOMOS is between approximately two percent and five percent of the dietary supplement by weight, although the relative percentage of BIOMOS could be increased to as much as ten percent if colonic ulcers are also being treated. The most preferred amount of BIOMOS is approximately two and one-half percent of the dietary supplement by weight.

The range of amounts of MYCOSORB is between approximately two percent and five percent of the dietary supplement by weight, although the relative percentage of MYCOSORB could be increased to as much as ten percent if colonic ulcers are being treated. The most preferred amount of MYCOSORB is approximately two and one-half percent of the dietary supplement by weight.

Next, the soluble fiber, which in the preferred embodiment is β-glucan, will be discussed. The range of amounts of β-glucan is between approximately ten percent and fifty percent of the dietary supplement by weight. The preferred amount of β-glucan is approximately fifteen to forty percent of the dietary supplement by weight. The most preferred amount of β-glucan is approximately thirty-six percent of the dietary supplement by weight.

The polar lipid supplement will now be discussed. It is apparent from the preceding discussion that the only non-solid ingredient in the dietary supplement of the present invention is the polar lipid supplement, which in the preferred embodiment is oat oil. Since the polar lipid supplement of the preferred embodiment consists of oat oil (which is the mixture of all three phases of oat oil), which is a liquid, it will be appreciated by those skilled in the art that by adding an additional amount of the third phase of oat oil, which is a thick paste, the resulting physical character of the polar lipid supplement will be varied, and by doing so, the resulting physical character of the dietary supplement in turn may also be varied. This variation is optional and is not done in the preferred embodiment.

As an example of this optional embodiment, by using relatively more oat oil and relatively less of the third phase of oat oil (or none of the third phase of oat oil at all), the dietary supplement will be thinner which will aid its administration using a dose syringe. On the other hand, by using relatively less oat oil and relatively more of the third phase of oat oil, the dietary supplement will be relatively thicker. Either of the two different formulations could be mixed with feed or encased in gelcaps. The range of each of the two ingredients in the polar lipid supplement is between approximately twenty and eighty percent by weight of the polar lipid supplement.

One preferred blend of the two ingredients in this optional embodiment of the polar lipid supplement is approximately sixty-two percent oat oil by weight, and approximately thirty-eight percent of the third phase of oat oil by weight. A second preferred blend of the two ingredients in the polar lipid supplement in this optional embodiment is that blend produced by the respective yields of the three phases of oat oil from oats. Since oats typically contain between twelve and sixteen percent oat oil by weight, and between five and six percent of the third phase of oat oil by weight, those skilled in the art will appreciate that this blend will be between twenty-four and thirty-three percent of the third phase of oat oil by weight.

The range of amounts of the polar lipid supplement in the dietary supplement of the present invention is between approximately twenty-nine percent and eighty percent of the dietary supplement by weight. The preferred amount of the polar lipid supplement is between approximately forty percent and sixty-five percent of the dietary supplement by weight. The most preferred amount of the polar lipid supplement is approximately fifty-two and one-half percent of the dietary supplement by weight.

For the preferred embodiment, the relative weight of the sodium bicarbonate is approximately two percent of the dietary supplement by weight.

The dietary supplement of the present invention may be administered either by adding it to feed or by feeding it directly as a dietary supplement. In the preferred embodiment, the dietary supplement is administered daily in order to maintain an optimal level of the ingredients in the animal's digestive tract. Alternately, it could instead be given more or less frequently so long as it is administered on a regular basis, although less frequent administration may not be as effective. It may be manufactured either as a liquid, in which case it can be added to feed which is then fed to a horse, or as a liquid or paste and stored in a gelatin capsule (as gelcaps), which makes for a consistent and uniform dosage of the dietary supplement. If manufactured as a paste, it can also be orally administered using a dose syringe.

Since the dietary supplement of the present invention slows the motility of foodstuffs through the digestive tract, it will be appreciated by those skilled in the art that by orally administering a medication in conjunction with the administration of the dietary supplement, the medication will also spend more time in the digestive tract. This will increase the absorption of the medication, and will likely thereby act to enhance the therapeutic effect of the medication. If desired, the medication can be administered at the same time the dietary supplement is administered, or even mixed or suspended in the dietary supplement prior to administration of the dietary supplement.

EXAMPLE

A clinical evaluation was made of the dietary supplement of the present invention. The formulation which was used was the preferred embodiment, which consisted of: thirty-two and one-half percent oat oil by weight; twenty percent of the third phase of oat oil by weight; thirty-six percent β-glucan by weight; two and one-half percent L-threonine by weight; two percent L-glutamine by weight; two and one-half percent BIOMOS by weight; two and one-half percent MYCOSORB by weight; and two percent sodium bicarbonate by weight.

The subjects of the clinical evaluation were eleven standard bred racehorses ranging in age from four to ten, with seven being geldings, two being stallions, and two being mares. At the beginning of the clinical evaluation, three of the horses had grade one ulcerations, one horse had grade one-two ulcerations, four horses had grade two ulcerations, and one horse had grade three ulcerations (as determined by examining them using an endoscope). In order to measure the performance of the horses prior to the clinical evaluation, the total earnings for each horse for the ten starts in races prior to beginning the clinical evaluation were obtained.

The horses were administered one ounce of the dietary supplement of the present invention once daily together with their hard feed (the grain diet which produces ulcerations), preferably at their evening feeding. Administration of the dietary supplement was with dose syringes, and the horses all willingly accepted the dietary supplement (with its oat base, the horses all liked its taste and willingly took it as a treat). No other change was made in the care and treatment of the horses. During the clinical evaluation, two of the horses were claimed, and one of the horses was not available for post-clinical evaluation analysis, leaving ten horses for which clinical data was obtained.

Therapeutic Results

All of the horses except one of the two which were claimed were checked for ulcerations (as determined by examining them using an endoscope). A random selection of four of the horses were checked eight weeks after beginning the clinical evaluation. Two of the horses checked at the eight-week check had not had ulcerations at the initiation of the clinical evaluation, and had no ulcerations at the eight-week check. One horse that had had grade one-two ulcerations had only scarring at the eight-week check, with the ulcerations having disappeared; this represented a substantial improvement. The other horse that had had grade three ulcerations had grade one ulcerations at the eight-week check, also a substantial improvement.

A final check of the ten horses remaining in the clinical evaluation for ulcerations (as determined using the endoscope) was made at sixteen weeks. The two horses that had not had ulcerations at the initiation of the clinical evaluation also had no ulcerations at the fifteen-week check. The horse that had had grade three ulcerations at the start of the clinical evaluation had no ulcerations at the sixteen-week check. Of the four horses which had had grade two ulcerations at the start of the clinical evaluation, two horses had improved to grade one ulcerations at the sixteen week check, two horses had improved to grade zero-one ulcerations at the sixteen week check, and one horse had no ulcerations at the sixteen week check. The horse that had had grade one-two ulcerations at the start of the clinical evaluation had no ulcerations at the sixteen-week check. Of the two horses that had had grade one ulcerations at the start of the clinical evaluation, one horses had improved to grade zero-one ulcerations at the sixteen-week check, and the other horse had no ulcerations at the sixteen-week check. Thus, all of the horses having ulcerations improved over the course of the sixteen-week clinical evaluation.

Performance Results

In addition, the horses consistently performed better after the initiation of the clinical evaluation than they had prior to the clinical evaluation, as measured by the total earnings for each horse for the ten starts in races subsequent to beginning the clinical evaluation. The average earnings for the horses were increased by sixty-three percent over their earnings for the ten races prior to initiation of the clinical evaluation. Even more remarkably, the two horses that were claimed during this period were claimed for over two hundred fifty percent of their assessed market value at the initiation of the clinical evaluation.

Blood Work Results

Complete blood work tests were run on all of the horses immediately prior to initiation of the clinical evaluation, and approximately every two weeks thereafter. The tests which were run were red blood cell count ("RBC"), hemoglobin ("HGB," which is a measure of the oxygen-carrying capacity of the blood), hematocrit ("HCT," which is the packed red blood cell volume), white blood cell count ("WBC"), Calcium, bicarbonate ("Bicarbo," which is the extrapolated pH of the blood), Chloride, and Total Protein. The results of each of these tests over an eight-week period are summarized herein.

The red blood cell count (RBC) is an indicator of athletic ability, and a general indication of the overall health of the horse. RBC readings from 6.8 to 12.9 are in the normal range. On average, for the eleven horses, RBC increased from 7.94 to 9.05, an indication of substantially increased athletic ability and enhanced health of the horses. The level of hemoglobin (HGB) is an indicator of the potential of the blood to carry oxygen, with higher numbers indicating a greater capacity and an enhanced athletic ability. HGB readings from 11 to 19 are in the normal range. On average, for the eleven horses, HGB increased from 13.1 to 15.1, an indication of substantially increased capacity and enhanced athletic ability.

The hematocrit (HCT) count is a measure of the percentage of blood volume made up of red blood cells. HCT readings from 38% to 42% are normal, with the lower and upper limits being 32% and 53%, respectively. On average, for the eleven horses, HCT was relatively unchanged, moving from 38.8% to 39%. The white blood cell count (WBC) is indicative of the status of the immune system and the general health of the horses. WBC readings from 5.4 to 14.3 are in the normal range. On average, for the eleven horses, WBC increased from 6.2 to 6.6, an indication of a healthy immune system and an enhanced level of general health of the horses.

Calcium is a measure of the level of calcium in the blood. Calcium readings from 10.8 to 12.5 are normal. On average, for the eleven horses, Calcium was relatively unchanged, moving from 11.6 to 11.5. Bicarbonate (Bicarbo) is the extrapolated pH of the blood. Bicarbo readings from 22 to 29 are normal, with a higher number being an important indicator of increased athletic efficiency of the horse due to its ability to neutralize lactic acid in the blood. On average, for the eleven horses, Bicarbo increased from 29 to nearly 31, an indication of substantially increased athletic capacity of the horses.

Chloride is used for electrical conduction of cells in the body. Chloride readings from 98 to 105 are normal, with an excessively low level presenting the potential of irregular heartbeats or a condition known as the "thumps" in which each heartbeat stimulates the diaphragm of the horse to flutter as well. On average, for the eleven horses, Chloride decreased only slightly from 100 to 98.9, representing an idiopathic phenomenon but one with no negative effect on the horses. Total Protein is the total amount of protein in the blood. Total Protein readings from 5.8 to 7.5 are normal. On average, for the eleven horses, Total Protein increased from 6.1 to 6.5, clearly demonstrating an enhanced level of absorption of nutrients which is indicative of improved function in the digestive tract.

The blood tests are entirely consistent with the therapeutic results and the performance results discussed above. The horses are demonstrably healthier as measured by four significant criteria, namely the red blood cell count (RBC), the level of hemoglobin (HGB), the level of Bicarbo, and the level of Total Protein. Further, these criteria indicate that the horses are likely to more athletic and better performing, a conclusion that has been confirmed by the performance results documented above.

Subjective Results

There is yet another indicator of the substantial benefit conferred on the horses through the use of the dietary supplement of the present invention. That indicator is the subjective observations of the trained horse professionals, including trainers, veterinarians, riders (including jockeys), and owners, as well as horse enthusiasts. The horses taking the dietary supplement were more active, appeared to be healthier (many people described the horses as having a "glow" which they had not previously had), and appeared to be more contented (no doubt due to the absence of ulcers). In addition, they were more responsive in the view of their trainers and jockeys. These subjective results coincided completely with the objective results discussed above. It will be readily apparent to those skilled in the art from the preceding discussion of the ingredients of the dietary supplement of the present invention and their interaction that the benefits achieved by the dietary supplement of the present invention is substantially greater than the sum of the benefits of each of the dietary supplement's ingredients separately.

It may therefore be appreciated from the above detailed description of the preferred embodiment of the present invention that it teaches a dietary supplement which efficaciously treats digestive tract ulcers in horses and, potentially, in other animals and even humans as well. The dietary supplement of the present invention can be fed to any animal including, but not limited to, avian, bovine, porcine, equine, ovine, caprine, canine, and feline species. In addition to having the effect of efficaciously treating digestive tract ulcers, the dietary supplement of the present invention demonstrates efficacy in the prevention of such digestive tract ulcers as well. The dietary supplement of the present invention is effective in treating and/or preventing gastric ulcers, and in treating colonic ulcers as well.

The dietary supplement of the present invention does not interfere with the proper digestion of foodstuffs while it is treating and/or preventing digestive tract ulcers. It consists entirely of safe and natural ingredients rather than drugs. The dietary supplement of the present invention is orally administrable, thereby making its dispensation a simple matter. It can also be packaged in single doses to make its administration as convenient as is possible.

The dietary supplement of the present invention is stable and has a long shelf life, and requires no special care to be provided by the user throughout its shelf life prior to usage. The dietary supplement of the present invention is also inexpensive relative to previously known dietary tract ulcer treatments, thereby enhancing its market appeal and affording it the broadest possible market. Finally, all of the aforesaid advantages and objectives of the dietary supplement of the present invention and its method of administration are achieved without incurring any substantial relative disadvantage.

Although the foregoing description of the dietary supplement of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A dietary supplement for use in treating digestive tract ulcers in horses, comprising:
   a polar lipid that has been isolated from its natural source which polar lipid strengthens the mucous gut membrane lining the inside wall of the stomach, wherein said polar lipid comprises oat oil;
   a soluble fiber source that has been fractionated from its natural origin which soluble fiber source is present in an amount that is effective to slow the passage of foodstuffs ingested together with the dietary supplement through the stomach; and
   a nutricine which increases the integrity of digestive tract membranes consisting of amino acids, wherein said amino acids include at least one of L-threonine or L-glutamine;
wherein said polar lipid, said soluble fiber source, and said nutricine are present in said dietary supplement in respective amounts sufficient to treat digestive tract ulcers in horses.

2. A dietary supplement as defined in claim 1, wherein said polar lipid contains antioxidants.

3. A dietary supplement as defined in claim 1, wherein said polar lipid additionally comprises at least one oil selected from the group consisting of soybean oil, olive oil, palm oil, sunflower oil, corn oil, rape seed oil, and linseed oil.

4. A dietary supplement as defined in claim 1, wherein said oat oil comprises a mixture of oat oil from all phases of a multi-phase oat extraction process.

5. A dietary supplement as defined in claim 1, wherein said polar lipid additionally comprises:
   oat oil from a last phase of the extraction process, said oat oil from the last phase of the extraction process being thick and having a relatively high viscosity.

6. A dietary supplement as defined in claim 5, wherein said polar lipid comprises:
   between approximately twenty percent and eighty percent oat oil from all phases of the extraction process by weight; and
   between approximately twenty percent and eighty percent oat oil from the last phase of the extraction process by weight.

7. A dietary supplement as defined in claim 6, wherein said polar lipid comprises:
   approximately sixty-two percent oat oil from all phases of the extraction process by weight; and
   approximately thirty-eight percent oat oil from the last phase of the extraction process by weight.

8. A dietary supplement as defined in claim 5, wherein said polar lipid comprises said oat oil and said oat oil from the last phase of the extraction process in a blend produced by their respective yields from oats.

9. A dietary supplement as defined in claim 1, wherein said polar lipid comprises between approximately twenty-nine percent and eighty percent of said dietary supplement by weight.

10. A dietary supplement as defined in claim 9, wherein said polar lipid comprises between approximately forty percent and sixty-five percent of said dietary supplement by weight.

11. A dietary supplement as defined in claim 10, wherein said polar lipid comprises approximately fifty-two and one-half percent of said dietary supplement by weight.

12. A dietary supplement as defined in claim 1, wherein said soluble fiber source is derived from at least one ingredient selected from the group consisting of oats, barley, and soybeans.

13. A dietary supplement as defined in claim 1, wherein said soluble fiber source is derived from oats.

14. A dietary supplement as defined in claim 1, wherein said soluble fiber source comprises:
   β-glucan (beta-glucan).

15. A dietary supplement as defined in claim 14, wherein said wherein said β-glucan is derived from oats.

16. A dietary supplement as defined in claim 1, wherein said soluble fiber source comprises between approximately ten and fifty percent of said dietary supplement by weight.

17. A dietary supplement as defined in claim 16, wherein said soluble fiber source comprises between approximately fifteen and forty percent of said dietary supplement by weight.

18. A dietary supplement as defined in claim 17, wherein said soluble fiber source comprises approximately thirty-six percent of said dietary supplement by weight.

19. A dietary supplement as defined in claim 1, wherein said amino acids comprise:
   L-threonine.

20. A dietary supplement as defined in claim 19, wherein said L-threonine comprises between approximately one percent and eight percent of said dietary supplement by weight.

21. A dietary supplement as defined in claim 20, wherein said L-threonine comprises approximately two and one-half percent of said dietary supplement by weight.

22. A dietary supplement as defined in claim 1, wherein said amino acids comprise:
   L-glutamine.

23. A dietary supplement as defined in claim 22, wherein said L-glutamine comprises between approximately one percent and five percent of said dietary supplement by weight.

24. A dietary supplement as defined in claim 23, wherein said L-glutamine comprises approximately two percent of said dietary supplement by weight.

25. A dietary supplement as defined in claim 1, additionally comprising:
   a second nutricine which absorbs and eliminates mycotoxins and/or pathogens in the digestive tract.

26. A dietary supplement as defined in claim 25, wherein said second nutricine that absorbs and eliminates mycotoxins and/or pathogens in the digestive tract comprises:
   a pathogenic bacteria absorbant.

27. A dietary supplement as defined in claim 26, wherein said pathogenic bacteria absorbant comprises between approximately two percent to five percent of said dietary supplement by weight.

28. A dietary supplement as defined in claim 27, wherein said pathogenic bacteria absorbant comprises approximately two and one-half percent of said dietary supplement by weight.

29. A dietary supplement as defined in claim 25, wherein said second nutricine that absorbs and eliminates mycotoxins and/or pathogens in the digestive tract comprises:
a mycotoxin absorbant.

30. A dietary supplement as defined in claim 29, wherein said mycotoxin absorbant comprises between approximately two percent to five percent of said dietary supplement by weight.

31. A dietary supplement as defined in claim 30, wherein said mycotoxin absorbant comprises approximately two and one-half percent of said dietary supplement by weight.

32. A dietary supplement as defined in claim 1, additionally comprising:
a pH balancer.

33. A dietary supplement as defined in claim 32, wherein said pH balancer comprises:
sodium bicarbonate.

34. A dietary supplement as defined in claim 32, wherein said pH balancer comprises a sufficient percentage of said dietary supplement to bring said dietary supplement to a neutral pH.

35. A dietary supplement as defined in claim 34, wherein said pH balancer comprises a sufficient percentage of said dietary supplement to bring said dietary supplement to a pH of approximately seven.

36. A dietary supplement as defined in claim 34, wherein said pH balancer comprises approximately two percent of said dietary supplement by weight.

37. A dietary supplement as defined in claim 1, additionally comprising:
a medication that is carried with the other ingredients of said dietary supplement, wherein at least one of the absorption or the therapeutic value of said medication is maximized by being taken in conjunction with said dietary supplement.

38. A feed supplement for use in treating digestive tract ulcers in horses, comprising:
an oat oil-based polar lipid that has been isolated from its natural source;
a β-glucan (beta-glucan) soluble fiber source that has been fractionated from its natural origin which β-glucan soluble fiber source is present in an amount that is effective to slow the passage of foodstuffs ingested together with the dietary supplement through the stomach;
a nutricine which increases the integrity of digestive tract membranes consisting of amino acids, wherein said amino acids include at least one of L-threonine or L-glutamine;
a second nutricine which absorbs mycotoxins and/or pathogens in the digestive tract; and
a pH balancer that is added to the other ingredients in the feed supplement to keep the pH of the feed supplement at an approximately neutral pH level;
wherein said polar lipid, said soluble fiber source, said nutricine, said second nutricine, and said pH balancer are present in said dietary supplement in respective amounts sufficient to treat digestive tract ulcers in horses.

39. A method of making a feed supplement for horses, said method comprising:
providing a polar lipid that has been isolated from its natural source, wherein said polar lipid comprises oat oil;
providing a soluble fiber source that has been fractionated from its natural origin which soluble fiber source is present in an amount that is effective to slow the passage of foodstuffs ingested together with the dietary supplement through the stomach;
providing a nutricine which increases the integrity of digestive tract membranes consisting of amino acids, wherein said amino acids include at least one of L-threonine or L-glutamine; and
mixing said polar lipid, said soluble fiber source, and said nutricine which increases the integrity of digestive tract membranes together;
wherein said polar lipid, said soluble fiber source, and said nutricine are present in said dietary supplement in respective amounts sufficient to treat digestive tract ulcers in horses.

40. A method of making a feed supplement for horses, said method comprising:
providing a polar lipid that has been isolated from its natural source, wherein said polar lipid comprises oat oil;
providing a soluble fiber source that has been fractionated from its natural origin which soluble fiber source is present in an amount that is effective to slow the passage of foodstuffs ingested together with the dietary supplement through the stomach;
providing a nutricine that increases the integrity of digestive tract membranes consisting of amino acids, wherein said amino acids include at least one of L-threonine or L-glutamine;
providing a second nutricine that absorbs mycotoxins and/or pathogens in the digestive tract;
mixing said polar lipid supplement, said soluble fiber source, said nutricine which increases the integrity of digestive tract membranes, and said second nutricine which absorbs mycotoxins and/or pathogens together; and
adding a pH balancer to the mixture of said polar lipid supplement, said soluble fiber source, said nutricine which increases the integrity of digestive tract membranes, and said second nutricine which absorbs mycotoxins and/or pathogens to keep the pH of the feed supplement at an approximately neutral pH level;
wherein said polar lipid, said soluble fiber source, said nutricine, said second nutricine, and said pH balancer are present in said dietary supplement in respective amounts sufficient to treat digestive tract ulcers in horses.

41. A method for feeding a dietary supplement for use in treating digestive tract ulcers in horses, said method comprising:
preparing an appropriately sized dose of dietary supplement comprising:
a polar lipid that has been isolated from its natural source, wherein said polar lipid comprises oat oil;
a soluble fiber source that has been fractionated from its natural origin which soluble fiber source is present in an amount that is effective to slow the passage of foodstuffs ingested together with the dietary supplement through the stomach; and
a nutricine which increases the integrity of digestive tract membranes consisting of amino acids, wherein said amino acids include at least one of L-threonine or L-glutamine;
administering said dietary supplement to a horse on a regular basis; and repeating said preparing and administering steps at least once daily;

wherein said polar lipid, said soluble fiber source, and said nutricine are present in said dietary supplement in respective amounts sufficient to treat digestive tract ulcers in horses.

42. A method for administering a medication in horses utilizing a dietary supplement for use in treating digestive tract ulcers in horses, said method comprising:

preparing an appropriately sized dose of dietary supplement comprising:

a polar lipid that has been isolated from its natural source which polar lipid is present which acts as a spreading agent to effectively coat the digestive tract with said dietary supplement, wherein said polar lipid comprises oat oil;

a soluble fiber source that has been fractionated from its natural origin which soluble fiber source is present in an amount that is effective to slow the passage of ingested items through the stomach; and a nutricine which increases the integrity of digestive tract membranes consisting of amino acids, wherein said amino acids include at least one of L-threonine or L-glutamine;

a second nutricine for absorbing and eliminating mycotoxins and/or pathogens in the digestive tract;

wherein said polar lipid, said soluble fiber source, said nutricine, and said second nutricine are present in said dietary supplement in respective amounts sufficient to treat digestive tract ulcers in horses;

mixing an appropriately sized dose of a medication into said dietary supplement; and administering said dietary supplement to a horse.

43. A method of treating digestive tract ulcers in horses, comprising:

preparing an appropriately sized dose of dietary supplement comprising:

a polar lipid that has been isolated from its natural source which polar lipid acts as a spreading agent to effectively coat the digestive tract with said dietary supplement, wherein said polar lipid comprises oat oil;

a soluble fiber source that has been fractionated from its natural origin which soluble fiber source is present in an amount that is effective to slow the passage of ingested items through the stomach;

a nutricine that increases the integrity of digestive tract membranes consisting of amino acids, wherein said amino acids include at least one of L-threonine or L-glutamine; and a second nutricine for absorbing and eliminating mycotoxins and/or pathogens in the digestive tract;

wherein said polar lipid, said soluble fiber source, said nutricine, and said second nutricine are present in said dietary supplement in respective amounts sufficient to treat digestive tract ulcers in horses; and administering said appropriately sized dose of dietary supplement to a horse.

* * * * *